United States Patent [19]

Mitchell

[11] Patent Number: 4,521,627

[45] Date of Patent: Jun. 4, 1985

[54] METHOD OF PREPARING ALKALI METAL SALTS OF ORGANIC DIAMINES

[75] Inventor: Peter W. D. Mitchell, Freehold, N.J.

[73] Assignee: Union Camp Corporation, Wayne, N.J.

[21] Appl. No.: 577,514

[22] Filed: Feb. 6, 1984

[51] Int. Cl.$^3$ .............................................. C07C 87/14
[52] U.S. Cl. .................................... 564/511; 564/368; 564/369; 564/372
[58] Field of Search ................ 564/511, 368, 369, 372

[56] References Cited

U.S. PATENT DOCUMENTS 3,234,277  2/1966  Beumel et al. ...................... 564/511

Primary Examiner—Charles F. Warren
Assistant Examiner—Joseph A. Boska
Attorney, Agent, or Firm—Kane, Dalsimer, Kane, Sullivan and Kurucz

[57] ABSTRACT

The disclosure is of a method of preparing alkaline metal salts of organic diamines. The method comprises, in brief, reacting the alkaline metal with a molar excess of the diamine in the presence of a catalytic proportion of a transition metal compound, at a temperature of from about 20° C. to reflux temperature for the reaction mixture.

5 Claims, No Drawings

METHOD OF PREPARING ALKALI METAL SALTS OF ORGANIC DIAMINES

BACKGROUND OF THE INVENTION

Field of the Invention

The invention relates to methods of preparing alkali metal salts of organic diamines.

BRIEF DESCRIPTION OF THE PRIOR ART

Alkali metal salts of amines are strongly basic reagents, useful for the isomerization of alkenes and alkynes, the dehydrogenation of cycloalkenes, and the cleavage of ethers. Reagents of particular interest are the alkali salts of ethylenediamine first reported by Reggel et al. [*J. Org. Chem.*, 23, 1136 (1958)] and the potassium salt of 1,3-diaminopropane first used by Brown [*J. Chem. Soc., Chem. Comm.*, 22 (1975)]. Of these reagents, only the lithium salts of ethylenediamine and 1,3-diaminopropane can be prepared directly by reacting lithium metal and diamine. The sodium and potassium derivatives cannot be made so directly. The normal practice in these cases is to first prepare sodium or potassium hydride and then to react the alkali metal hydride with the diamine. This is a complicated and expensive procedure.

Furthermore, even the lithium reagents which can be prepared directly are of limited usefulness because of the prohibitive cost and relative scarcity of the metal itself. It is much more desirable to have a direct means for preparing the sodium derivatives since sodium is an inexpensive metal, readily available on a very large commercial scale.

SUMMARY OF THE INVENTION

The invention comprises a method of preparing alkali metal salts of organic diamines, which comprises, reacting said metal with a molar excess of said diamine in the presence of a catalytic proportion of a transition metal compound at a temperature of from about 20° C. to reflux temperature of the reaction mixture.

The term "alkali metal" is used herein in its normally accepted sense as embracive of lithium, sodium, potassium, rubidium and cesium.

DETAILED DESCRIPTION OF THE PREFERRED EMBODIMENTS OF THE INVENTION

The method of the present invention may be employed to form the alkali metal salt of an organic diamine particularly the sodium and potassium salts directly from reaction of an alkali metal and an organic diamine in the presence of a catalyst.

Representative of such diamines are those of the formula:

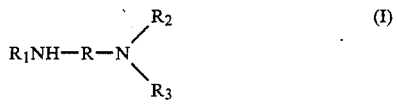

wherein R represents alkylene of 2 to 10 carbons, inclusive; and $R_1$, $R_2$ and $R_3$ are each independently selected from the group consisting of hydrogen, alkyl of 1 to 20 carbons, inclusive, aminoalkyl, phenyl, and aralkyl of 7 to 20 carbons, inclusive.

The term "alkylene of 2 to 10 carbons" as used throughout the specification and claims means the divalent moiety obtained upon removal of two hydrogen atoms from a hydrocarbon having the stated carbon content. Representative of 2 to 10 carbons are ethylene, propylene, butylene, pentylene, hexylene, heptylene, octylene, nonylene, decylene and isomeric forms thereof.

The term "alkyl of 1 to 20 carbons, inclusive" as used herein means the monovalent moiety obtained upon removal of a single hydrogen atom from a hydrocarbon. Representative of alkyl having 1 to 20 carbon atoms is methyl, ethyl, propyl, butyl, pentyl, hexyl, heptyl, octyl, nonyl, decyl, undecyl, dodecyl, tridecyl, tetradecyl, pentadecyl, heptadecyl, octadecyl, nonadecyl, eicosyl, heneiscosyl and isomeric forms thereof.

The term "aminoalkyl" as used herein means alkyl as defined above wherein a hydrogen atom has been replaced by an amino group. Representative of aminoalkyl are aminomethyl, aminoethyl, aminopropyl, aminobutyl, aminooctadecyl, aminotricosyl, aminopentacosyl and the like.

The term "aralkyl of 7 to 20 carbons, inclusive" means the monovalent moiety obtained upon the removal of a hydrogen atom from the alkane portion of an aralkane. Representative of aralkyl of 7 to 20 carbons, inclusive, are benzyl, phenethyl, phenpropyl, phenbutyl, phenhexyl, napthoctyl and the like.

Organic diamines of the formula (I) given above are generally well known compounds as are methods of their preparation. Representative of the organic diamines of the formula (I) are ethylenediamine, 1,3-diaminopropane, 1,4-diaminobutane, 1,6-hexamethylene diamine, diethylenetriamine, triethylenetetramine, 3,3'-diamino-N-methyldipropylamine, and the like.

The method of the invention is advantageously carried out by bringing the reactants together in any conventional reaction vessel, preferably adapted to stir the reaction mixture, to control the resulting exothermic reaction, and to vent hydrogen gas evolved. The reactants may be all mixed together or the metal may be added to a molar excess of the organic diamine and catalyst over a period of time to control the resulting exotherm. Generally, the term "molar excess of organic diamine" is used to mean that 1.1 to 10 moles of the organic diamine is used in the reaction mixture for each mole of the metal reactant added to the reaction mixture, preferably 3 to 4 moles of diamine for each mole of metal.

The desired reaction can be carried out at a temperature within the range of from about 20° C. to reflux temperature for the diamine. It is usually initiated by heat and a reaction temperature of about 80° C. is preferred.

Although the reaction described above may be carried out at atmospheric, sub- or super-atmospheric pressures, atmospheric pressures are convenient. It is preferred to carry out the reaction in an atmosphere free of oxygen and moisture, materials which react rapidly with alkali metals and their diamine salts, for example, an atmosphere of high-purity nitrogen or helium.

Critical to the method of the invention is the presence of a catalytic proportion of a transition metal compound during the above-mentioned reaction. In general, a catalytic proportion is within the range of from about 0.001 to 10 weight percent, preferably about 1 to 5 weight percent of the alkali metal reactant.

Transition metal compounds are generally well known materials as are methods of their preparation.

Preferred catalysts for the above-mentioned reaction are compounds of manganese, iron, nickel, cobalt, copper, platinum and palladium. The form of the metal does not seem to be critical, it is believed that the first step in the reaction is reduction of the catalyst and deposition on the surface of the alkali metal of a fine, activated form of transition metal. Representative of preferred catalysts are ferric chloride, iron oxide, iron pentacarbonyl, cobalt chloride, nickel bromide, nickel acetylacetonate, manganese acetate, cupric chloride, potassium hexachloropalatinate, palladium chloride, palladium-on-carbon, and the like. The most preferred catalysts are ferric chloride and palladium chloride.

The completion of the above-described reaction is indicated by a cessation of the evolution of hydrogen gas and by the complete disappearance of solid alkali metal. At the conclusion of the reaction, the desired salt may be separated by conventional technique such as by distillation of the diamine or by precipitation and filtration.

The following examples describe the manner and process of making and using the invention and set forth the best mode contemplated by the inventor of carrying out the invention but are not to be construed as limiting.

EXAMPLE 1

Anhydrous ferric chloride (35 mg) was added to ethylenediamine (7.8 g) in a 50 ml flask under an atmosphere of dry nitrogen. Sodium metal (0.75 g) was then added and the reaction mixture warmed with stirring. At about 50° C. black patches appeared on the surface of the sodium and gas evolution began. At 80° C. gas evolution was vigorous and the reaction mixture turned brown. Dissolution of the sodium was complete after 1 hour at 80° C.

EXAMPLE 2

Following the procedure of Example 1, potassium metal (1.50 g) was added to a mixture of ferric chloride (70 mg) and 1,3-diaminopropane (9.62 g). Reaction set in at ambient temperature and was complete after 1 hour at 60° C., giving a brown solution.

EXAMPLE 3

Following the procedure of Example 1, sodium metal (about 1 g) was stirred with ethylenediamine (about 8 g) and a variety of compounds containing transition metals. The results, shown in the Table, demonstrate that Groups VII-B, VIII and I-B metal-containing compounds are active catalysts.

TABLE

| Catalyst | Reaction Time (hrs) | Reaction Temperature (°C.) | Result |
| --- | --- | --- | --- |
| $NiBr_2$ | 1 | 90 | complete dissolution |
| $CoCl_2.6H_2O$ | 1 | 90 | complete dissolution |
| $Fe(CO)_5$ | 1 | 80 | complete dissolution |
| $Fe_2O_3$ | 1 | 80 | complete dissolution |
| Ni(acetylacetonate)$_2$ | 1 | 80 | complete dissolution |
| Pd $Cl_2$ | 0.5 | 90 | complete dissolution |
| 5% Pd—on-C | 1 | 80 | complete dissolution |
| K Pt $Cl_6$ | 2 | 90 | complete dissolution |
| Cr(acetylacetonate)$_3$ | 2 | 100 | no reaction |
| Zn $Cl_2$ | 2 | 75 | no reaction |
| Hg $Cl_2$ | 2 | 70 | no reaction |
| Mn(OAc)$_2$.4H$_2$O | 2 | 75 | nearly complete dissolution |
| CuCl | 2 | 95 | nearly complete dissolution |
| None | 24 | 100 | no reaction |

What is claimed:

1. A method of preparing alkali metal salts of organic diamines, which comprises; reacting said metal with a molar excess of said diamine in the presence of a catalytic proportion of a transition metal compound at a temperature of from about 20° C. to reflux temperature for the reaction mixture.

2. The method of claim 1 wherein the alkali metal is sodium or potassium.

3. The method of claim 2 wherein the diamine is ethylenediamine or 1,3-diaminopropane.

4. The method of claim 2 wherein the transition metal in the catalytic compound is selected from the group consisting of manganese, iron, cobalt, nickel, copper, platinum and palladium.

5. The method of claim 2 wherein the transition metal compound is a compound of iron or palladium.

* * * * *